US010869956B2

(12) United States Patent
Torrance et al.

(10) Patent No.: US 10,869,956 B2
(45) Date of Patent: Dec. 22, 2020

(54) INTERVENTIONAL CATHETERS INCORPORATING ASPIRATION AND/OR INFUSION SYSTEMS

(71) Applicant: BOSTON SCIENTIFIC LIMITED, Hamilton (BM)

(72) Inventors: Casey Torrance, Seattle, WA (US); Kate Walsh, Kirkland, WA (US); Jared Salstrom, Renton, WA (US); Scott Youmans, Bothell, WA (US); Edward I. Wulfman, Woodinville, WA (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 147 days.

(21) Appl. No.: 16/001,722

(22) Filed: Jun. 6, 2018

(65) Prior Publication Data

US 2018/0280594 A1 Oct. 4, 2018

Related U.S. Application Data

(60) Continuation of application No. 15/052,248, filed on Feb. 24, 2016, now Pat. No. 10,010,657, which is a
(Continued)

(51) Int. Cl.
*A61M 1/00* (2006.01)
*A61M 31/00* (2006.01)
(Continued)

(52) U.S. Cl.
CPC ....... *A61M 1/0084* (2013.01); *A61B 1/00087* (2013.01); *A61B 1/05* (2013.01);
(Continued)

(58) Field of Classification Search
CPC ...... A61B 17/3207; A61B 2017/22079; A61B 2017/320775; A61B 2217/005;
(Continued)

(56) References Cited

U.S. PATENT DOCUMENTS

| 4,728,319 A | 3/1988 | Masch |
| 4,981,467 A | 1/1991 | Bobo, Jr. et al. |

(Continued)

FOREIGN PATENT DOCUMENTS

| WO | 9521576 A1 | 8/1995 |
| WO | 2004080345 A2 | 9/2004 |

(Continued)

OTHER PUBLICATIONS

European Patent Office, EP 07843776 Supplementary European Search Report, dated Nov. 17, 2009.

*Primary Examiner* — Rebecca E Eisenberg
(74) *Attorney, Agent, or Firm* — Seager, Tufte & Wickhem LLP (57) ABSTRACT

An interventional catheter assembly comprising a catheter for insertion and guidance to a target site in a body lumen or a cavity and an operating head mounted in proximity to a distal end of the catheter and comprising a system for removing obstructive material from the target site is provided. In certain embodiments, the catheter assembly includes at least one aspiration port located proximal to the operating head that communicates with a first sealed lumen for withdrawing fluids and obstructive material from the target site. The catheter assembly may also include at least one liquid infusion port that communicates with a second sealed lumen for supplying fluid to a location in proximity to the target site. Kits including the interventional catheter assembly with an aspiration and/or infusion conduit are also provided.

19 Claims, 3 Drawing Sheets

Related U.S. Application Data continuation of application No. 14/179,441, filed on Feb. 12, 2014, now Pat. No. 9,295,373, which is a division of application No. 12/957,236, filed on Nov. 30, 2010, now Pat. No. 8,657,785, which is a division of application No. 11/866,973, filed on Oct. 3, 2007, now Pat. No. 7,842,009.

(60) Provisional application No. 60/894,173, filed on Mar. 9, 2007, provisional application No. 60/828,209, filed on Oct. 4, 2006.

(51) Int. Cl.
| | |
|---|---|
| *A61M 37/00* | (2006.01) |
| *A61B 17/3207* | (2006.01) |
| *A61B 1/00* | (2006.01) |
| *A61B 1/05* | (2006.01) |
| *A61B 8/12* | (2006.01) |
| *A61B 8/00* | (2006.01) |
| *A61M 25/09* | (2006.01) |
| *A61M 5/142* | (2006.01) |
| *A61M 5/168* | (2006.01) |
| *A61M 25/00* | (2006.01) |
| *A61B 17/32* | (2006.01) |
| *A61B 17/22* | (2006.01) |

(52) U.S. Cl.
CPC ............... *A61B 8/12* (2013.01); *A61B 8/445* (2013.01); *A61B 17/32002* (2013.01); *A61B 17/3207* (2013.01); *A61B 17/320725* (2013.01); *A61B 17/320758* (2013.01); *A61M 1/0023* (2013.01); *A61M 1/0058* (2013.01); *A61M 1/0066* (2013.01); *A61M 5/142* (2013.01); *A61M 5/16831* (2013.01); *A61M 25/0082* (2013.01); *A61M 25/09* (2013.01); *A61B 2017/22079* (2013.01); *A61B 2017/320004* (2013.01); *A61B 2017/320032* (2013.01); *A61B 2017/320775* (2013.01); *A61B 2217/005* (2013.01); *A61B 2217/007* (2013.01)

(58) Field of Classification Search
CPC ............... A61B 2217/007; A61B 8/12; A61B 17/32002; A61M 1/0058; A61M 1/0066; A61M 25/0082; A61M 5/142
See application file for complete search history.

(56) References Cited

U.S. PATENT DOCUMENTS

| | | | |
|---|---|---|---|
| 5,030,201 | A | 7/1991 | Palestrant |
| 5,074,841 | A | 12/1991 | Ademovic et al. |
| 5,078,722 | A | 1/1992 | Stevens |
| 5,261,877 | A | 11/1993 | Fine et al. |
| 5,284,486 | A | 2/1994 | Kotula et al. |
| 5,358,485 | A | 10/1994 | Vance et al. |
| 5,370,609 | A | 12/1994 | Drasler et al. |
| 5,417,703 | A | 5/1995 | Brown et al. |
| 5,569,275 | A | 10/1996 | Kotula et al. |
| 5,779,721 | A | 7/1998 | Nash |
| 5,876,414 | A | 3/1999 | Straub |
| 5,938,670 | A | 8/1999 | Keith et al. |
| 6,001,112 | A | 12/1999 | Taylor |
| 6,053,923 | A | 4/2000 | Veca et al. |
| 6,063,069 | A | 5/2000 | Cragg et al. |
| 6,238,405 | B1 | 5/2001 | Findlay, III et al. |
| 6,454,775 | B1 | 9/2002 | Demarais et al. |
| 6,503,261 | B1 | 1/2003 | Bruneau et al. |
| 6,524,323 | B1 | 2/2003 | Nash et al. |
| 6,565,588 | B1 | 5/2003 | Clement |
| 6,666,874 | B2 | 12/2003 | Heitzmann et al. |
| 6,702,830 | B1 | 3/2004 | Demarais et al. |
| 6,818,001 | B2 | 11/2004 | Wulfman et al. |
| 6,843,797 | B2 | 1/2005 | Nash et al. |
| 6,905,505 | B2 | 6/2005 | Nash et al. |
| 7,344,546 | B2 | 3/2008 | Wulfman |
| 7,981,128 | B2 | 7/2011 | To et al. |
| 8,007,506 | B2 | 8/2011 | To et al. |
| 8,361,094 | B2 | 1/2013 | To et al. |
| 8,657,785 | B2 | 2/2014 | Torrance et al. |
| 2002/0007190 | A1 | 1/2002 | Wulfman et al. |
| 2002/0016564 | A1 | 2/2002 | Courtney et al. |
| 2002/0169467 | A1 | 11/2002 | Heitzmann et al. |
| 2004/0006358 | A1 | 1/2004 | Wulfman et al. |
| 2004/0181249 | A1 | 9/2004 | Torrance et al. |
| 2004/0220519 | A1 | 11/2004 | Wulfman et al. |
| 2004/0243162 | A1 | 12/2004 | Wulfman et al. |
| 2005/0085769 | A1 | 4/2005 | MacMahon et al. |
| 2005/0169968 | A1* | 8/2005 | Elmaleh ............... C08L 59/00 424/426 |
| 2005/0240146 | A1 | 10/2005 | Nash et al. |
| 2007/0073233 | A1 | 3/2007 | Thor et al. |
| 2007/0118072 | A1 | 5/2007 | Nash |
| 2007/0179435 | A1 | 8/2007 | Braig et al. |
| 2008/0103439 | A1 | 5/2008 | Torrance et al. |

FOREIGN PATENT DOCUMENTS

| | | |
|---|---|---|
| WO | 2004080507 A2 | 9/2004 |
| WO | 2006058223 A2 | 6/2006 |
| WO | 2007055850 A2 | 5/2007 |

* cited by examiner

INTERVENTIONAL CATHETERS INCORPORATING ASPIRATION AND/OR INFUSION SYSTEMS

CROSS-REFERENCE TO RELATED APPLICATIONS

This application is a continuation application of U.S. patent application Ser. No. 15/052,248, filed Feb. 24, 2016, which is a continuation of U.S. patent application Ser. No. 14/179,441, filed Feb. 12, 2014, now U.S. Pat. No. 9,295,373, which is a divisional of U.S. patent application Ser. No. 12/957,236, filed Nov. 30, 2010, now U.S. Pat. No. 8,657,785, which is a divisional of U.S. patent application Ser. No. 11/866,973, filed Oct. 3, 2007, now U.S. Pat. No. 7,842,009, which claims priority to U.S. Provisional Patent Application Nos. 60/894,173 filed Mar. 9, 2007, and 60/828,209 filed Oct. 4, 2006. The disclosures of these priority applications are incorporated by reference herein in their entireties.

TECHNICAL FIELD

The present invention relates to methods and systems for removing material, such as obstructions and partial obstructions, from an internal lumen or cavity of a mammalian subject, such as a blood vessel. More particularly, the present invention relates to interventional catheters having operating heads incorporating aspiration and/or infusion systems for withdrawal of liquids and debris from a site of intervention and introduction of fluids to the site.

BACKGROUND

Removal of disease such as atherosclerotic plaque, thrombus and other types of obstructions and partial obstructions from internal body lumens or cavities using advanceable, rotating operating heads having cutter assemblies or abrasive materials is a well-established interventional technique. Numerous interventional catheters have been conceived and developed. Most of these systems require placement of a guide wire and guiding catheter prior to introduction of the interventional catheter and placement of the interventional catheter at the target operating site. Many of these prior art systems incorporate vacuum aspiration systems to remove the ablated material from the site, thereby preventing distal embolization. Some interventional catheters additionally or alternatively incorporate or are used in conjunction with other mechanisms, such as distal filters, for preventing removed material from circulating in the blood stream. Numerous interventional catheters also provide infusion of a liquid to the site of the intervention. Infused liquids may assist in the material removal process, or may be provided as diagnostic or therapeutic materials prior to, during or following an intervention.

Devices for collecting undesired material from a site in a body lumen or cavity, such as a blood vessel, that employ material excision devices incorporating a blade, barb, screw, or another material capture mechanism, to draw material into a device cavity are also known. These material capture mechanisms may be provided on a non-rotating or a rotating operating head. Non-cutting and non-mechanical systems for removing material from body lumens and blood vessels, such as heat, ultrasound and laser ablation systems, have also been developed.

Despite the many and varied approaches to the material removal systems, many challenges remain in providing systems for removing material from a lumen, such as a blood vessel, safely and reliably and without causing complications. The safety and reliability of the system is manifestly critical. Recovery of debris generated during a material removal operation, or reducing the particle size of the debris to a particle size that will not damage blood vessels or produce embolic events, is essential. The flexibility and size of an interventional catheter are also important features. The system must be small enough and flexible enough to navigate through sometimes tortuous internal structures and passageways for placement at the target interventional site. Maintaining desired fluid infusion rates and pressures, system flexibility and effective aspiration capacity while withdrawing debris through a long, small diameter catheter presents numerous challenges.

SUMMARY

The present invention provides interventional catheters that may be employed to rapidly and effectively remove unwanted material from body lumens or cavities. Interventional catheters and control systems disclosed herein may be adapted for use within a variety of body lumens or cavities such as blood vessels and vascular cavities, gastrointestinal cavities, lumens or cavities in the urinary system and in male and female reproductive organs, and other fluid cavities such as pulmonary lumens and gas exchange cavities, nasal and sinus cavities and the like. The lumen or cavity may form a generally tubular structure, such as a blood vessel, a ureter, a fallopian tube, a nasal passageway, and other tubular passageways. For example, systems of the present invention may be used for removing undesired material from native blood vessels such as native coronary, renal, cranial, peripheral and other blood vessels, artificial or grafted vessels such as saphenous vein grafts, and the like. The lumen may have implanted devices such as stents in place. The lumen or cavity may be within, or in proximity to, an organ such as a kidney, gall bladder, lung or the like, or the body cavity may form part of another system, such as a lymph node, spinal canal, or the like. Interventional catheters are generally used to remove unwanted material from a target site in body lumens or cavities of mammalian subjects, particularly human patients.

The undesired material that is removed using interventional catheter assemblies and control systems disclosed herein may be disease material such as atherosclerotic plaque, calcified plaque, thrombus, or other types of deposits, gallstones, a valve or portion thereof, and the like. In certain embodiments, the interventional catheter assemblies disclosed herein are employed in the treatment of cardiovascular or peripheral artery disease (PAD) to remove disease material from blood vessels, including peripheral blood vessels.

The present interventional catheter assembly includes a catheter system that is at least partially inserted and navigated within a patient's body while an operator controls the system externally of the patient's body. A control module housing aspiration and/or infusion systems, providing power to a downstream interventional catheter controller, and providing various control and display features may also be provided. The interventional catheters disclosed herein incorporate a material removal component, referred to herein as an "operating head," which is generally positioned at or near the distal end of the interventional catheter system. As used herein, "proximal" refers to a direction toward the system controls and the operator along the path of the catheter system, and "distal" refers to the direction away from the system controls and the operator along the path of the catheter system toward or beyond a terminal end of the operating head.

Fluidic communication between the operating head and externally positioned components of the interventional catheter system is generally provided by one or more sealed passageways of the catheter system. Other types of communication systems or pathways may also be provided for delivery of power, for rotationally driving and translating the operating head, for implementing various control features, and the like. The operating head may be driven, or controlled, using electrical systems, radio frequency and other remote control systems, mechanical systems, magnetic systems and other systems or modalities suitable for remote operation of an operating head. The operating head may also incorporate features providing additional functionalities such as ultrasound guidance, various types of imaging features, and the like. The system components described below are described as exemplary components and are not intended to limit the scope of the invention.

The interventional catheter system may be used in conjunction with a flexible guidewire that is navigated through internal pathways, such as blood vessels, to a target material removal site. For partial obstructions, the guidewire is generally placed across the lesion and the operating head of the interventional catheter is advanced on the guidewire to the target site and then operated into and through the lesion. When a lumen is totally obstructed and a guidewire cannot penetrate the obstruction without causing harm to nearby tissue or risking embolization, the operating head may be advanced beyond the distal tip of the guidewire and into and through the obstruction, or the operating head and guidewire may be advanced in tandem. Other methods that may be employed for guiding and steering the operating head include, but are not limited to, radio frequency systems, stereotactic systems, magnetic systems, remote control systems, and the like. The interventional catheters disclosed herein may be adapted for use with any of these steering systems.

The operating head may take any of a variety of forms. In one embodiment, the operating head is rotatable and incorporates cutter elements. Rotational operating heads are generally operably connected to a rotatable drive shaft and catheter system, and drive system and control systems and, in embodiments described herein, comprise at least one distally located cutter assembly, wherein the cutter assembly includes at least one cutting, or scraping or abrading surface, referred to as a cutting surface or blade. Although the "cutting" or "cutter" surfaces or blades of an interventional catheter of the present invention may be sharp and may actually "cut" material at the target site, the term "cut" or "cutting" or "cutter" or "blade(s)," as used herein, refers to cutting, scraping, abrading, ablating, macerating and otherwise breaking down undesired material into particles or smaller, removable, units of material.

In some embodiments, interventional catheters incorporate cutter assemblies comprising a plurality of cutting blades and may incorporate fixed and/or adjustable blades. Suitable cutter assemblies are disclosed, for example, in U.S. Pat. Nos. 6,565,588 and 6,818,001, which are incorporated herein by reference in their entireties. Differential cutting blades are preferred for use in many applications and suitable differential cutting blades are disclosed, for example, in U.S. Patent Publication 2004/0006358 A1, which is incorporated herein by reference in its entirety. In some embodiments, the operating head may comprise an abrasive surface or an abrasive material provided on a surface of a blade or another rotational element. Rotational elements incorporating abrasives are well known in the art. In an alternative embodiment, the operating head may comprise another type of ablation device, such as a plaque excision device, a laser ablation or high frequency ultrasound ablation device, or a radio frequency or heat-producing or electrical device that operates to remove unwanted material from body lumens or cavities and generally does not rotate during operation. These ablation devices are also well known in the art.

In applications employing rotational operating heads, the drive shaft that conveys rotation and torque from a drive system to the operating head is small enough and flexible enough to be navigated through small and tortuous passageways during navigation of the operating head to the target removal site. It also has sufficient mechanical integrity to transfer high rotational and torque loads, and operate in a high vacuum, or aspirate withdrawal, environment. Multifilar helical coils are used as drive shafts in many types of interventional catheters having a rotatable operating head. Suitable drive shafts are well known in the art and are described in the patent publications incorporated herein by reference.

The drive shaft is carried in a flexible catheter structure and mounted, directly or indirectly, to the operating head to rotate the operating head. The rotational operating head and drive shaft may be directly or indirectly connected to the flexible catheter structure by means of a bearing near the distal end, such that the catheter remains stationary during operation of the operating head, while the operating head is rotated by the drive shaft. Alternatively, the operating head and drive shaft may be independent of the catheter at its distal end, such that the operating head is rotatable and axially translatable independent of the catheter assembly.

Interventional catheters disclosed herein preferably incorporate an aspiration system for removal of debris from the intervention site by means of aspiration through one or more aspiration ports. Aspiration systems suitable for use in interventional catheters of the present invention are described, for example, in the patents incorporated herein by reference and in U.S. Patent Publication 2004/0220519 A1, which is also incorporated herein by reference in its entirety. Debris generated during a material removal operation is entrained in fluids (e.g. blood), and the aspirate fluid containing debris is removed through the material removal port(s) and withdrawn through a sealed lumen of the interventional catheter.

In one embodiment of interventional catheters of the present invention, at least one large aspiration port is provided in proximity to, and preferably proximal to, the operating head. Debris generated during a material removal operation is entrained in fluids (e.g. blood), and the aspirate fluid containing debris is withdrawn through the proximal aspiration port(s) and conveyed through a sealed lumen of the interventional catheter to an aspirate conduit for discharge in an aspirate collection system. Additional, generally smaller, material removal ports may also be disposed on one or more surfaces of the operating head itself.

Liquid infusion may also be provided in proximity to the operating head. Infusion of liquids may be used to provide additional liquid volume for removal of debris, or to deliver lubricating fluids, diagnostic or treatment agents, contrast agents and the like. Infusion of fluids such as saline in proximity to the target material removal area may be desirable because it tends to reduce the viscosity of the materials being removed, thus facilitating removal through relatively small diameter lumens. Infusion of liquids also desirably tends to reduce the volume of blood removed during a material removal operation, thereby reducing blood loss and allowing longer procedures. In addition, infusion of liquids reduces vessel collapse and keeps the vessel wall in tension, thereby improving the effectiveness of cutting operations and reducing damage to the vessel wall. Liquid infusion may also reduce guidewire friction in embodiments where guidewires are employed. Liquid infusion may be provided distal or proximal to the operating head, and/or may be provided through the operating head.

Many different types of infusion systems are known and may be used in interventional catheters of the present invention. In one embodiment, multiple infusion ports are arranged to provide a substantially even distribution of infusate around the circumference of the device, while in alternative embodiments, one or more infusion ports may be provided to distribute infusate in a directed manner at one or more locations around the circumference of the device. A plurality of fluid infusion ports are provided in an outer sheath mounted over a distal catheter portion and positioned proximal to the operating head in one embodiment. Infusion may additionally or alternatively be provided through ports in the operating head.

In general, interventional catheters of the present invention operate to provide a volume ratio of infusate to aspirate of greater than about 1:1. For example, the volume ratio of infusate to aspirate may greater than 1.5:1 and less than about 2.5:1. Infusion and aspiration rates may also be controlled within desired ranges, and several monitoring and control features may be provided. In one embodiment, for example, a bubble detection mechanism is provided to detect a bubble in the infusion conduit and inactivate the infusion pump and/or power to the operating head upon detection of a bubble. In another embodiment, the infusion and aspiration systems are activated automatically upon activation of the operating head, or after a delay period following activation of the operating head. In yet another embodiment, the infusion and aspiration systems are may also be inactivated automatically upon inactivation of the operating head, or after a delay period following inactivation of the operating head.

DETAILED DESCRIPTION

Certain preferred embodiments are described herein with reference to a material removal device having a rotating operating head that removes undesired material using a cutting mechanism. It will be appreciated that this device embodiment is being described as illustrative and that the inventions and features disclosed herein are applicable to interventional catheters having different types of operating heads, including generally static operating heads using non-cutting mechanisms of material removal.

Figure 1:
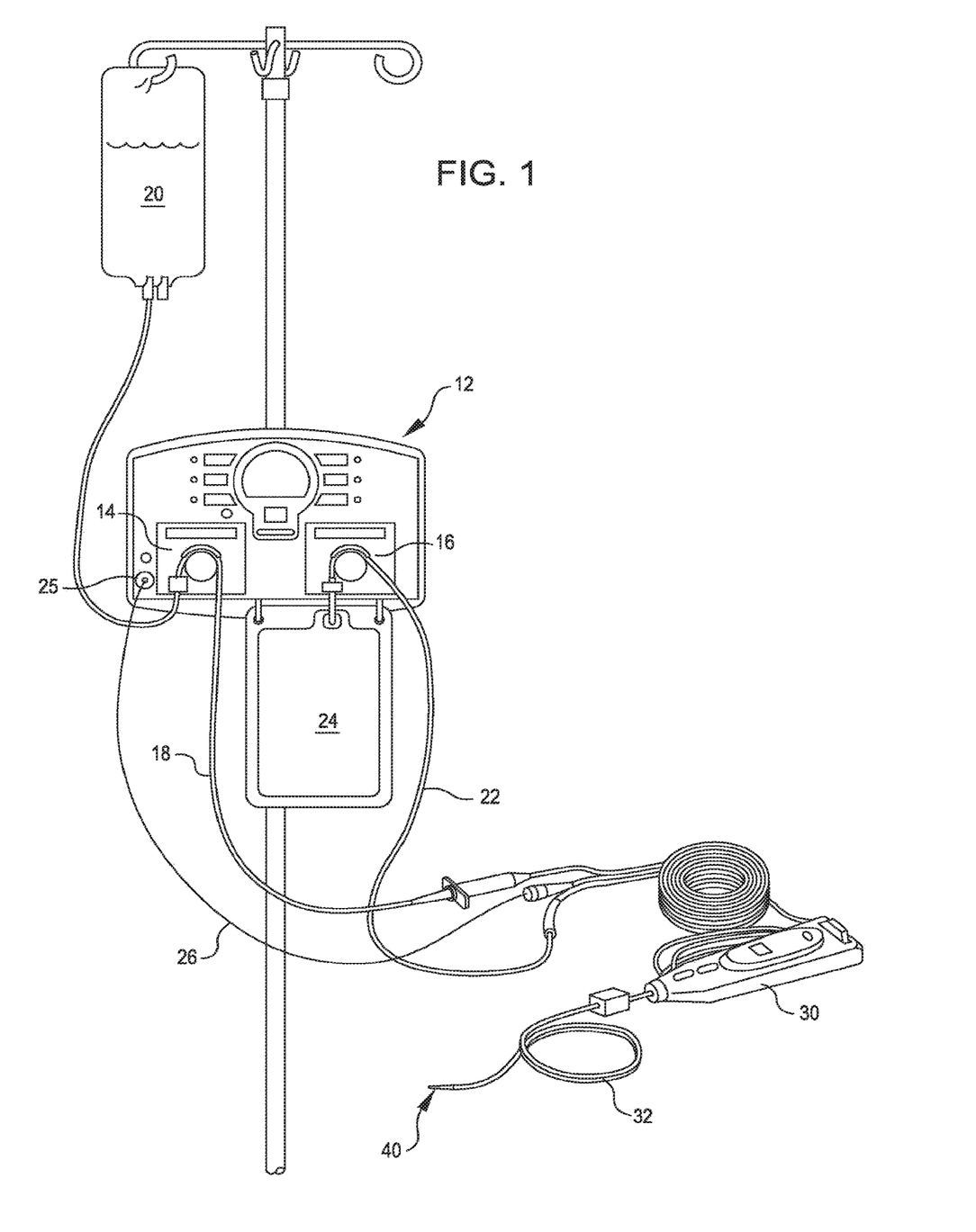
FIG. 1 is a schematic diagram of an interventional catheter assembly having aspiration and infusion systems and comprising an operating head mounted at or near a distal end of a catheter system, a controller and a console unit.

FIG. 1 illustrates an exemplary embodiment of an interventional catheter assembly, including a console unit incorporating aspiration and infusion systems as disclosed herein. Interventional catheter assembly 10 comprises console unit 12, controller 30, and catheter system 32 having an operating head 40 located at or in proximity to the distal end of the catheter system. Controller 30 may be used to manipulate (e.g. advance and/or rotate) the catheter system 32 and operating head 40, or alternative controls may be provided. The configuration of the operating head and aspiration and infusion ports provided in association with the operating head will be described below with reference to FIGS. 2 and 3.

Console unit 12 incorporates an infusion pump 14 and an aspiration pump 16. During operation of the interventional catheter, an infusate conduit 18 draws fluid from an infusate reservoir 20 and operably contacts the infusion pump 14 to provide fluid through an infusion lumen in catheter system 32 to one or more infusion ports provided in proximity to the operating head. Similarly but in reverse, fluids with entrained particulates are withdrawn from the site of intervention through an aspiration lumen in catheter system 32 and conveyed to aspiration conduit 22, which is in operable contact with the aspiration pump 16, and communicates with the aspirate collection vessel 24. Console unit 12 may also provide a power source for operating the operating head and system components, or it may be in communication with an external power source. In the illustrated embodiment, console unit 12 provides power to the interventional catheter assembly and controller 30 by means of a device power port 25 and power cord 26.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 12. Console unit 12 is generally provided as a reusable assembly and is generally operated outside the sterile field. It may be mountable on a portable stand to facilitate convenient placement during interventions.

One function of console unit 12 is to provide feedback of system and/or environmental conditions or operating parameters. The console unit may output operational information concerning operating conditions and feedback from the material removal site to the operator. According to one embodiment, console unit 12 provides continuously updated output to an operator of operating parameters such as operating head rotation rate, which may include the actual run speed as well as the desired speed; operating head advance rate; aspiration rate and/or volume; infusion rate and/or volume; length of the body or matter to be removed that is traversed; and the like.

Certain automated and selectable control features may be implemented in console unit 12. Preset routines or programs involving various operating parameters may be preselected, stored and selectable by an operator, for example. Thus, according to one embodiment, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as: cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

High efficiency aspiration is important in the interventional catheter systems disclosed herein. In certain embodiments, fluid and associated particulates are aspirated from the intervention site at rates of at least 15 ml/min of operating head run time and, in many embodiments, fluid and associated particulates are aspirated at rates of at least 25 ml/min of operating head run-time. In exemplary interventional catheter systems, the aspiration site may be more than a meter away from the controller 30 through an aspirate removal passageway located within the catheter system 32 and having a diameter of less than 0.10 inch, for example between about 0.050 to 0.070 inch. The distance that the aspirate travels between controller 30 and console unit 12 may be from about ½ meter to several meters, through an aspirate conduit that is between about 0.125 to about 1.0 inch in diameter. The blood and debris being aspirated are relatively viscous fluids, and achieving a relatively constant and high level of aspiration under these conditions is essential.

In one embodiment, aspiration pump 16 comprises a multi-lobed roller pump. The rotation rates of multiple rollers, or of a multi-lobed rotating structure, may be variable or selectable to control the aspiration rate and volume. Roller pumps permit fluid to flow in a conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. For example, a collection bag 24 and a sealed aspiration conduit may be provided as part of a sterile disposable interventional catheter kit. A distal end of the aspiration conduit may be pre-mounted on and sealed to the controller 30. A proximal portion of the aspiration conduit is mounted on the aspiration pump prior to operation of the interventional catheter and the aspirate collection bag is mounted to or in proximity to the control module.

Infusion pump 14 may also comprise a multi-lobed roller pump employing variable or selectable rotation rates to control the infusion rate and volume. A simple bag or another infusate reservoir, such as those used for intravenous infusions, may be used to supply the infusate. For example, an infusate reservoir 20 having a sealed conduit that is mounted in the infusion pump 16 during operation of the interventional catheter may be provided. In this embodiment, the sealed infusate conduit may be provided as part of the sterile disposable interventional catheter system and a distal end of the infusate conduit may be pre-mounted on and sealed to the controller 30. A proximal portion of the infusate conduit may be connected to an infusate reservoir, such as a saline bag, and mounted in proximity to the infusion pump prior to operation. A bubble detector 15 may be provided in association with console unit 12 and infusate conduit 18 to detect the presence of gas bubbles in the infusate. A control feature that automatically disables the infusion pump and/or power to the operating head may be activated upon detection of a fault (e.g. a bubble) in the infusate conduit.

Console unit 12 may also have control switches for activating and shutting down the aspiration pump and system, and for activating and shutting down the infusion pump and system. These control features may be provided as simple on/off switches. Alternatively, systems providing different levels or rates of aspiration and/or infusion that are selectable by an operator may be provided. In addition, console unit 12 may be provided with a timing mechanism that determines, and displays, the elapsed time of operation of the operating head and/or the aspiration and infusion systems. The volumes of aspirate withdrawn and the volume of infusate introduced may also be detected and displayed by console unit 12. Detection systems for monitoring the levels of aspirate and infusate in the respective reservoirs may be incorporated and alarms indicating an overfill condition for the aspirate collection system or a low supply condition for the infusate reservoir may be provided. Back-up aspirate collection and infusate supply systems may also be provided.

In one embodiment, console unit 12, together with aspiration pump 16, infusion pump 14 and the associated control and display features, is provided as a separate, reusable unit, that may be used as standard equipment in operating rooms, for example. In the system illustrated, console unit 12 is not contaminated by contact with blood or aspirate during operation, and the power and control systems are durable and long-lasting and may be reused for many interventions. Console unit 12 may be provided in a housing designed to sit on a platform during operation, or the housing may be designed for mounting on a portable structure, such as an i.v. pole or another structure. The interventional catheter system, comprising the catheter system 32 with operating head 40, the controller 30, aspirate conduit 22, aspirate collection vessel 24, and infusate conduit 18 may be provided as a sterile, single use system kit.

The catheter system and operating head are described below with a reference to a rotatable operating head employing a cutting material removal mechanism. In this application, aspiration and infusion conduits terminate at or within controller 30, where they communicate with aspiration and infusion lumens within the catheter system 32. A rotatable drive shaft for driving the operating head is provided in catheter system 32. A guidewire may also transit controller 30 and catheter system 32. In general, controller 30 or an associated control mechanism provides user-operated mechanisms for rotating and/or translating the operating head. Controller 30, which is constructed from a durable, sterilizable material, such as hard plastic, may be provided in any convenient ergonomic design and constructed for placement in proximity to and/or in contact with the external body. In one embodiment, the controller may include an integrated handle for operator convenience in holding and supporting the controller during operation. Catheter system 32, exiting controller 30, is axially translatable with respect to controller 30 as the operating head and catheter system are guided to a target material removal site. It will be appreciated that some of the control and operational features described herein with reference to controller 30 may be provided in console unit 12 and, likewise, some of the control and operational features described with reference to console unit 12 may be provided in controller 30.

The operating head 40 of the interventional catheter disclosed herein may comprise any of a variety of rotational cutting devices or assemblies having one or more cutting surface(s) for cutting, fragmentizing, pulverizing, ablating, scraping, grinding or otherwise reducing the size of undesired material and/or separating undesired material from healthy tissue, such as the walls of a blood vessel, in proximity to the target removal site. Differential cutter assemblies may be provided, as described in the U.S. patent publications incorporated herein by reference. Operating heads comprising abrasive rotational surfaces may also be used. The operating head, or sub-components thereof, such as the cutting surfaces, may be coated with a radio-opaque material such as gold, platinum, inks and the like, to render the operating head radioscopically visible and to assist a medical professional in guiding and positioning the cutter assembly relative to an occlusion.

Figure 2:
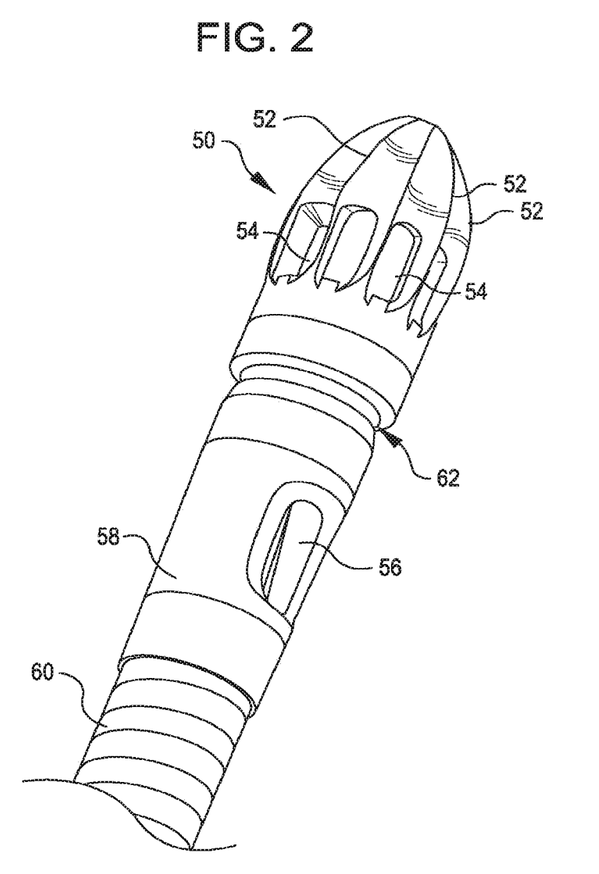
FIG. 2 is an enlarged diagram illustrating the distal end of an interventional catheter of the present invention incorporating an operating head with aspiration and/or infusion ports and a proximal port for aspiration and/or infusion.

FIG. 2 illustrates the distal end of one embodiment of an interventional catheter of the present invention. In this embodiment, the operating head comprises a multi-bladed cutter assembly 50 having a plurality of raised blades 52 arranged in a radially symmetrical configuration. Blades 52 are preferably differential cutting blades, and cutting assembly 50 may incorporate a plurality of ports 54 arranged in a radially symmetrical configuration in the spaces between blades 52. Ports 54 are shown provided between each set of neighboring blade structures in FIG. 2, but it will be appreciated that fewer ports may be provided. Ports 54 are preferably provided in a generally proximal portion of cutter assembly 50 and may have a generally oblong configuration, as illustrated, or may take a variety of other configurations.

The distal end of the interventional catheter illustrated in FIG. 2 additionally comprises a large port 56 located in a distal portion of the catheter, or a proximal portion of the cutter assembly, proximal to blades 52. Port 56 is generally provided as a window or cut-out in a cylindrical structure and preferably spans at least 10% of the circumference of the structure; more preferably at least 20% the circumference of the structure; and yet more preferably at least 30% the circumference of the structure. The cylindrical structure supporting port 56 may be a distal catheter portion, or port 56 may be provided in a generally cylindrical tubular structure mounted, directly or indirectly, to a distal catheter portion 60. In one embodiment, illustrated in FIG. 2, a rigid cylindrical shell 58 is mounted to distal catheter portion 60 at its proximal end and is mounted to or forms a stationary element of bearing 62 at its distal end. Bearing 62 allows distal catheter portion 60 and cylindrical shell 58 to remain stationary during rotation of cutting assembly 50. Bearing 62 may also provide limited articulation of cutting assembly 50 about its longitudinal axis.

In the embodiment illustrated in FIG. 2, ports 54 may be operated as aspiration or infusion ports and, likewise, enlarged proximal port 56 may be operated as an aspiration or infusion port. In one embodiment, proximal port 56 is provided as an aspiration port and communicates with an aspiration lumen within catheter 60 that communicates with aspiration conduit 22, while ports 54 operate as infusion ports and communicate with an infusion lumen within catheter 60 that communicates with infusion conduit 26. In another embodiment, port 56 is provided as an infusion port and communicates with an infusion lumen within catheter 60 that communicates with infusion conduit 26, while ports 54 operate as aspiration ports and communicate with an aspiration lumen within catheter 60 that communicates with aspiration infusion conduit 22.

Figure 3:
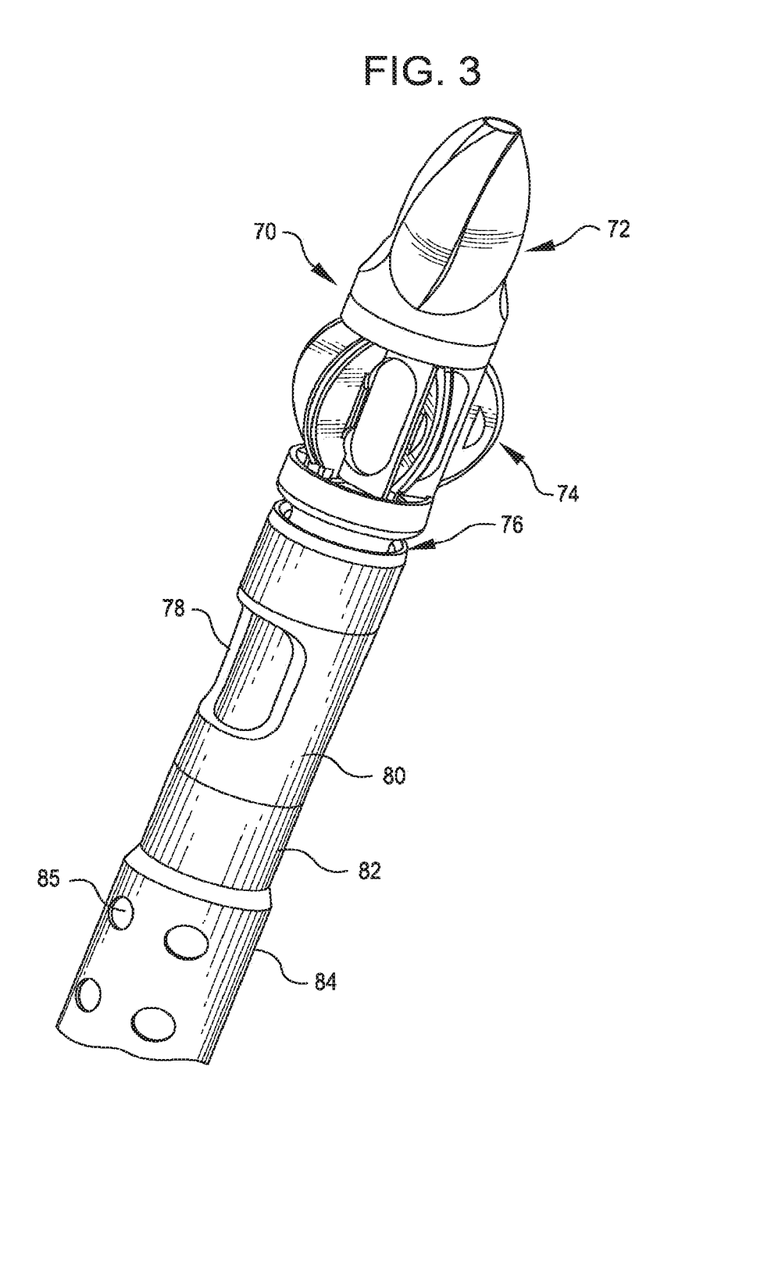
FIG. 3 is an enlarged diagram illustrating the distal end of an interventional catheter of the present invention incorporating an operating head, an aspiration port located proximally of the operating head, and a plurality of infusion ports located proximally to the aspiration port.

In another embodiment of an interventional catheter of the present invention illustrated in FIG. 3, operating head 70 comprises a distal cutter assembly 72 and a proximal cutter assembly 74 mounted to a bearing system 76 that allows rotation of the operating head while the catheter components proximal to the operating head remain stationary. The interventional catheter illustrated in FIG. 3 additionally comprises a proximal aspiration port 78 provided as an opening in a cylindrical structure located proximal to cutter assemblies 72 and 74. Aspiration port 78 communicates with an aspiration lumen within catheter 82 that communicates proximally with aspiration conduit 22. Proximal port 78 may be provided as an opening or window in a distal catheter portion, or it may be provided as an opening in a substantially rigid cylindrical shell 80. Cylindrical shell 80 is constructed of a generally rigid, durable material, such as surgical steel or stainless steel, and has a length that is approximately the same as that of each of the cutter assemblies. Shell 80 is generally mounted to, or forms a stationary component of, bearing 76 at its distal end. Bearing 76 allows catheter 82 and cylindrical casing 80 to remain stationary during rotation of operating head 50. Bearing 76 may also provide limited articulation of operating head 70 about its longitudinal axis.

Aspiration port 78 may be provided as a window spanning at least 15% of the circumference of the shell structure; more preferably at least 25% of the circumference of the shell structure; yet more preferably at least 35% of the circumference of the shell structure. The proximal aspiration port may be provided in a generally ovoid, rectangular, or square profile. In certain embodiments, aspiration port 78, which may be generally oval in shape, has an opening, or surface area that is between about 0.5 to about 20 mm.sup.2, preferably between about 0.5 and 10 mm.sup.2 in surface area.

The interventional catheter illustrated in FIG. 3 additionally incorporates a plurality of infusion ports 85 located proximally with respect to aspiration port 78, but in proximity to the aspiration port and operating head 70. Infusion ports 85, which may be provided in an outer sheath 84, as shown in FIG. 3, communicate with an infusion lumen in the catheter assembly, which communicates with infusion conduit 26. In certain embodiments, between two and twenty, for example twelve, infusion ports 85 are provided in an infusion sheath 84 mounted to distal catheter 82. The infusion ports may have a generally uniform size, or infusion ports of different sizes may be provided. The infusion ports may be generally cylindrical, as shown in FIG. 3, or they may have alternative configurations. Each infusion port 85 may have a diameter of approximately 0.005 in. to 0.20 in., more preferably from about 0.006 in. to about 0.015 in. Infusion ports having diameters of about 0.010 in. are especially preferred for certain applications. In one embodiment, the infusion ports are spaced in a generally circumferential pattern to provide a substantially uniform flow of infusate around the circumference of the infusion sheath.

In an alternative embodiment, a single infusion port having a surface area generally equal to or less than the surface area of the aspiration port may be provided proximally to the aspiration port. A plurality of infusion ports may also be spaced relatively closely and arranged to provide targeted infusion, resulting in a higher volume or pressure of infusate at different locations around the circumference of the infusion sheath. Providing a large infusion port, or a series of infusion ports in close proximity to one another allows directional flow of infusate and may facilitate aspiration of debris and/or positioning of the operating head.

In certain embodiments, the infusion rate and pressure is relatively low, unlike many prior art systems in which a high rate of fluid infusion is employed to break-up unwanted material or to guide an operating head. In many embodiments, for example, the pressure of the infusion fluid as measured at the infusion pump may from about 80 to 200 psi. The volume ratio of infusate to aspirate is also important in many applications. In systems of the present invention, the rate of infusion is generally greater than the rate of aspiration. For example, the volume ratio of infusate to aspirate may be greater than about 1:1 and less than about 3:1. For some applications, the volume ratio of infusate to aspirate may be greater than about 1.5:1 and less than about 2.5:1. In some embodiments, the volume ratio of infusate to aspirate is approximately 1.5:1, 2:1 or 2.5:1. In certain embodiments, the rate of infusion is approximately 45-100 ml/min of device run-time, and the rate of aspiration is approximately 20-60 ml/min of device run-time. In certain embodiments, the rate of infusion is approximately 45-150 ml/min, for example 50-90 ml/min, of device run-time, and the rate of aspiration is approximately 20-90 ml/min, for example, 20-60 ml/min of device run-time.

Various control and feedback mechanisms may be used in connection with the aspiration and infusion systems in interventional catheters of the present invention. In one embodiment, for example, a bubble detection device is provided in proximity to an infusate conduit and operates to detect gas bubbles in the infusate fluid. An alarm may be triggered upon detection of a bubble, or a control mechanism may inactivate the infusion and aspiration systems in response to detection of a bubble. Power to the operating head may also be inactivated upon detection of a bubble to inactivate the system and prevent introduction of the bubble into the patient.

Activation and inactivation of the infusion and aspiration systems may be controlled by an operator using operator selectable features and controls. Alternatively, various operating protocols may be programmed into the system or provided as selectable features. Operation of the aspiration and infusion systems may be coordinated in a variety of ways, for example, with operation of the operating head. Activation and inactivation of the operating head is generally controlled by the operator. In one embodiment, the infusion system is primed to ensure that the infusate conduit is filled with liquid and a reliable supply of infusate to infusion ports in proximity to the operating head is established prior to guidance of the interventional catheter to the site of intervention. In one embodiment, the infusate and aspiration systems are activated automatically upon activation of the operating head. In another embodiment, the infusate and aspiration systems are activated after a generally short delay period following activation of the operating head. The infusion and aspiration systems may also be inactivated automatically upon inactivation of the operating head. Alternatively, the infusion and/or aspiration systems may be inactivated after a predetermined or selectable time period following inactivation of the operating head. The system may optionally incorporate override controls that allow an operator to override a programmed infusion or aspiration feature.

The present invention has been described with reference to specific device embodiments and figures. These specific embodiments should not be construed as limitations on the scope of the invention, but merely as illustrations of exemplary embodiments. It is further understood that many modifications, additions and substitutions may be made to the described interventional catheter and control system without departing from the scope of the present invention.

What is claimed is:

1. An interventional catheter assembly comprising:
   an operating head mounted at a distal end of a catheter assembly configured for removing obstructive material from a target site in a body lumen or a cavity;
   an infusion pump operably connected to a fluid infusion system for delivery of an infusate fluid through the catheter assembly to the target site in the body lumen or cavity;
   a detector for detecting a presence of a bubble in the infusate fluid; and
   a control module operatively connected to the infusion pump and the operating head;
   wherein upon detection of a bubble in the infusate fluid, the control module inactivates the infusion pump;
   wherein upon detection of the presence of a bubble in the infusate fluid, the control module inactivates the operating head.

2. The interventional catheter assembly of claim 1, wherein the control module automatically activates the fluid infusion system upon activation of the operating head.

3. The interventional catheter assembly of claim 1, additionally comprising at least one override control that allows an operator to override a pre-programmed infusion feature.

4. The interventional catheter assembly of claim 1, wherein a pressure of the infusate fluid as measured at the infusion pump is about 80 to 200 psi.

5. The interventional catheter assembly of claim 1, further comprising an aspiration pump operably connected to a fluid aspiration system for aspiration of fluid in proximity to the operating head.

6. The interventional catheter assembly of claim 5, wherein the control module automatically activates the fluid aspiration system and the fluid infusion system upon activation of the operating head.

7. The interventional catheter assembly of claim 5, wherein the control module automatically inactivates the fluid aspiration system and the fluid infusion system after a selected time period following inactivation of the operating head.

8. The interventional catheter assembly of claim 5, further comprising an infusion port for supplying infusate fluid to a location in proximity to the target site.

9. The interventional catheter assembly of claim 8, further comprising an aspiration port in proximity to the operating head for aspirating fluids and obstructive material from the target site.

10. The interventional catheter assembly of claim 9, wherein the aspiration port is located proximal to the operating head.

11. The interventional catheter assembly of claim 10, wherein the infusion port is located proximal of the aspiration port.

12. An interventional catheter assembly comprising:
   an operating head mounted at a distal end of a catheter assembly configured for removing obstructive material from a target site in a body lumen or a cavity;
   an infusion pump operably connected to a fluid infusion system for delivery of an infusate fluid through the catheter assembly to the target site in the body lumen or cavity;
   a detector for detecting a presence of a bubble in the infusate fluid; and a control module operatively connected to the infusion pump and the operating head;

wherein upon detection of a bubble in the infusate fluid, the control module inactivates the infusion pump;

wherein the control module automatically inactivates the fluid infusion system after a selected time period following inactivation of the operating head.

13. The interventional catheter assembly of claim 12, wherein upon detection of the presence of a bubble in the infusate fluid, the control module inactivates the operating head.

14. An interventional catheter system, comprising:

an operating head mounted at a distal end of a catheter assembly configured for removing obstructive material from a target site in a body lumen or a cavity;

an aspiration system including an aspiration pump for applying vacuum to an aspiration port disposed proximate the operating head;

an infusion system including an infusion pump for delivery of an infusate fluid through the catheter assembly to a target site in a body lumen or cavity through an infusion port disposed proximal of the aspiration port, wherein the aspiration port is located proximal to the operating head; and a detector disposed in proximity to an infusate conduit for detecting a presence of a bubble in the infusate fluid;

wherein upon detection of the presence of the bubble in the infusate fluid, a control module inactivates the aspiration system and the infusion system.

15. The interventional catheter system of claim 14, wherein upon detection of the presence of the bubble in the infusate fluid, the control module inactivates the operating head.

16. The interventional catheter system of claim 14, wherein the control module automatically activates the infusion system upon activation of the operating head.

17. The interventional catheter system of claim 14, wherein the control module automatically activates the aspiration system upon activation of the operating head.

18. The interventional catheter system of claim 14, wherein the control module automatically activates the infusion system and the aspiration system after a predetermined period of time following activation of the operating head.

19. The interventional catheter system of claim 14, wherein the control module automatically inactivates the infusion system and the aspiration system after a predetermined period of time following inactivation of the operating head.

* * * * *